United States Patent [19]

Michaels

[11] 4,367,741

[45] Jan. 11, 1983

[54] DISPENSER POWERED BY CROSS-LINKED HYDROPHILIC POLYMER GRAFTED TO HYDROPHILIC POLYMER

[75] Inventor: Alan S. Michaels, San Francisco, Calif.

[73] Assignee: Alza Corporation, Palo Alto, Calif.

[21] Appl. No.: 218,729

[22] Filed: Dec. 22, 1980

[51] Int. Cl.³ .............................................. A61M 7/00
[52] U.S. Cl. ................................................. 128/260
[58] Field of Search ................. 128/260, 261; 222/95, 222/386.5

[56] References Cited

U.S. PATENT DOCUMENTS

| 3,865,108 | 2/1975 | Hartop | 128/260 |
| 4,203,440 | 5/1980 | Theeuwes | 128/260 |
| 4,203,442 | 5/1980 | Michaels | 128/260 |
| 4,223,061 | 9/1980 | Michaels | 128/260 |
| 4,304,232 | 12/1981 | Michaels | 128/260 |

*Primary Examiner*—C. Fred Rosenbaum
*Attorney, Agent, or Firm*—Paul L. Sabatine; Edward L. Mandell

[57] ABSTRACT

A dispenser is disclosed comprising a housing formed of a laminate of a cross-linked hydrophilic polymer layer grafted to a noncross-linked hydrophilic layer. The housing surrounds a container made of an elastomeric material and the container has an outlet through the housing to the exterior of the dispenser.

12 Claims, 5 Drawing Figures

DISPENSER POWERED BY CROSS-LINKED HYDROPHILIC POLYMER GRAFTED TO HYDROPHILIC POLYMER

FIELD OF THE INVENTION

This invention relates to a dispenser powered by a laminate comprising (1) a layer of a cross-linked hydrophilic polymer grafted to (2) a layer of a noncross-linked hydrophilic polymer.

THE PRIOR ART

Various forms of energy have been used for powering dispensers for delivering beneficial agents to environments of use. For example, U.S. Pat. No. 3,760,984 issued to patentee Theeuwes discloses a dispenser comprising an inner chamber formed of a heat shrinkable polymer carrying on its outer surface an osmotic solute and a distant layer of a polymer permeable to fluid. The dispenser has a means for filling the chamber. The dispenser is powered by fluid being imbibed into the dispenser, wherein it dissolves the solute, thereby forming a solution that exerts pressure against the chamber, causing it to shrink and deliver agent from the dispenser. In U.S. Pat. No. 3,865,108, Hartop discloses a dispenser consisting of a base formed of an expandable material, with a hole in the base for holding a receptable. The dispenser is powered by the base absorbing fluid and expanding, which expansion squeezes the receptable causing it to collapse and deliver agent from the dispenser. In U.S. Pat. No. 3,987,790, Eckenhoff et al disclose an improvement in an osmotic dispenser consisting of a conduit for filling a bag in the dispenser. The dispenser is powered by an osmotically effective solute imbibing fluid into the dispenser, which fluid generates hydraulic pressure applied against the bag, causing it to squeeze inwardly forcing agent from the dispenser. In U.S. Pat. No. 3,971,376, Wichterle discloses a dispenser consisting of a capsule having unitary walls formed of a gel material swellable in fluids. A textile fabric is imbedded in the material for imparting strength and minimizing problems due to poor mechanical properties associated with the material that occur during fluid uptake used to power the dispenser. In U.S. Pat. No. 3,995,631, Higuchi et al. disclose a bag bearing on its outer surface a layer of an osmotic solute, and a distant wall formed of a material having part controlled permeability to fluid. In operation, a solution is formed of the solute, which solution squeezes the bag and delivers agent from the dispenser. In copending U.S. Application Ser. No. 06/115,750, now U.S. Pat. No. 4,304,232, applicant Michaels discloses a dispenser comprising a wall that governs the passage of fluid into the dispenser, a container that can change in volume and has a passageway dimensioned for controlling the rate of release from the container, and a lamina formed of a material that absorbs fluid and is positioned between the wall and the container. The dispenser delivers agent by the combined integrated operations of the wall, the lamina, the container, and the passageway acting in unison for urging agent from the dispenser.

While the above dispensers are useful for delivering numerous agents to many environments of use, and while the dispensers represent a major advancement in the dispensing art, it will be appreciated by those versed in the art, there are instances where a dispenser made with an inventively novel improvement would also enjoy a wide use and application in the dispensing art. For example, if a dispenser is made from a wall forming material that combines both constructional integrity and stored energy for powering the dispenser, thereby providing an improvement in the dispenser, by advancing the structural design and enhancing the operability of the dispenser, while simultaneously reducing the number of steps needed to make the dispenser, such a dispenser would have immediate acceptance, and it also would represent a valuable contribution in the fields of science and commerce.

OBJECTS OF THE INVENTION

Accordingly, it is an immediate object of this invention to provide a novel dispenser for delivering fluids and beneficial agents to environments of use, and which dispenser represents an improvement in the dispenser art.

Yet another object of the invention is to provide a dispenser comprising a wall that imparts structure and shape to the dispenser and which wall is also a potential source of energy for powering the dispenser.

Still another object of the invention is to provide a dispenser that is self-powered in fluid environments, is easy to manufacture, and can be used for dispensing beneficial agents to animals, including humans, and to other biological and non-biological environments of use.

Yet still another object of the invention is to provide a dispenser comprising a wall for absorbing fluid, and retaining a significant fraction of the fluid for increasing its dimensions, which increase can be used as a mechanical driving power for delivering an agent from the dispenser.

Another object of the invention is to provide a dispenser that is empty until filled, and when filled can administer a complete pharmaceutical dosage regimen for a period of time, the use of which requires intervention only for the initiation and the termination of the regimen.

Another object of the invention is to provide a dispenser fabricated with a wall that can function in a plurality of fluid environments.

It is a further object of the invention to provide a novel dispenser, which can operate to yield results substantially equivalent to those obtained with sustained release methods of drug administration.

Other objects, features and advantages of the invention will be apparent to those skilled in the art, from the detailed description of the specification, taken in conjunction with the drawings, and the accompanying claims.

SUMMARY OF THE INVENTION

The invention concerns a dispenser for delivering a fluid or an agent to an environment of use. The dispenser in a presently preferred embodiment is manufactured as a dispensing device especially designed for dispensing drug to a biological environment. The dispenser comprises a wall formed of a laminate comprising (1) a layer of a cross-linked hydrophilic polymer grafted to (2) a layer of a noncross-linked hydrophilic polymer. The wall-laminate surrounds an inner collapsible container made of an elastomeric material, which houses a fluid, or a useful agent composition. In operation, the dispenser releases fluid or agent in response to the wall-laminate absorbing fluid from the environment and expanding, thereby exerting pressure on the container which collapses and ejects fluid or agent from the dispenser.

BRIEF DESCRIPTION OF THE DRAWINGS

In the drawings, which are not drawn to scale, but are set-forth to illustrate various embodiments of the invention, the figures are as follows.

In the drawings and the specification, like parts in related Figures are identified by like numbers. The terms appearing earlier in the specification, and in the description of the drawings, as well as embodiments thereof, are further described elsewhere in the disclosure.

DETAILED DESCRIPTION OF THE DRAWINGS

Figure 1:
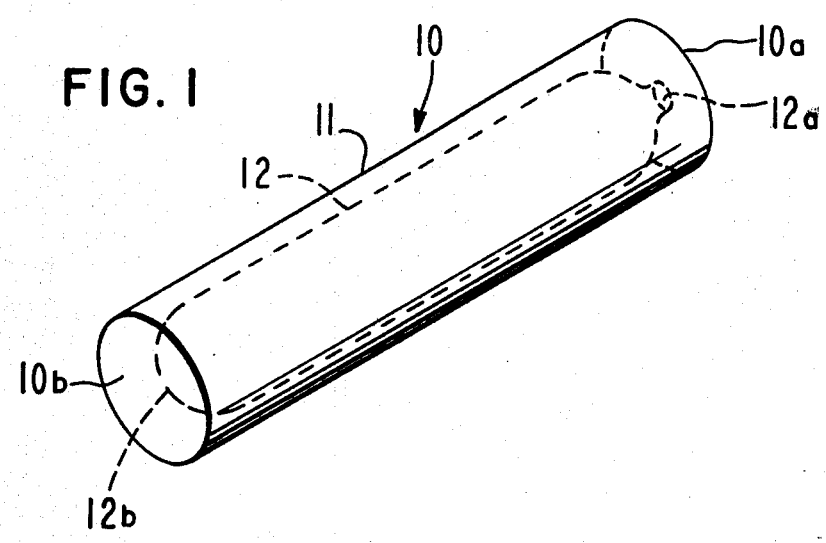
FIG. 1 is a side view illustrating a dispenser made according to the invention.

Turning now to the drawings in detail, which are an example of a new and useful dispenser for dispensing a fluid, or a fluid containing a useful agent, including drug, and which example is not to be construed as limiting, one dispenser is illustrated in FIG. 1 by the numeral 10. In FIG. 1, dispenser 10 has a lead end 10a and a rear end 10b, with dispenser 10 sized, shaped and adapted for placing and retaining dispenser 10 in a preselected environment of use. Dispenser 10 comprises wall 11, a housing that surrounds and defines an internal space, not seen in FIG. 1, for housing a container 12, illustrated by a broken line. Container 12 has a passageway 12a, an outlet means for dispensing a fluid or an agent, and container 12 has a rear end 12b that fits against the rear of wall 11.

Figure 2:
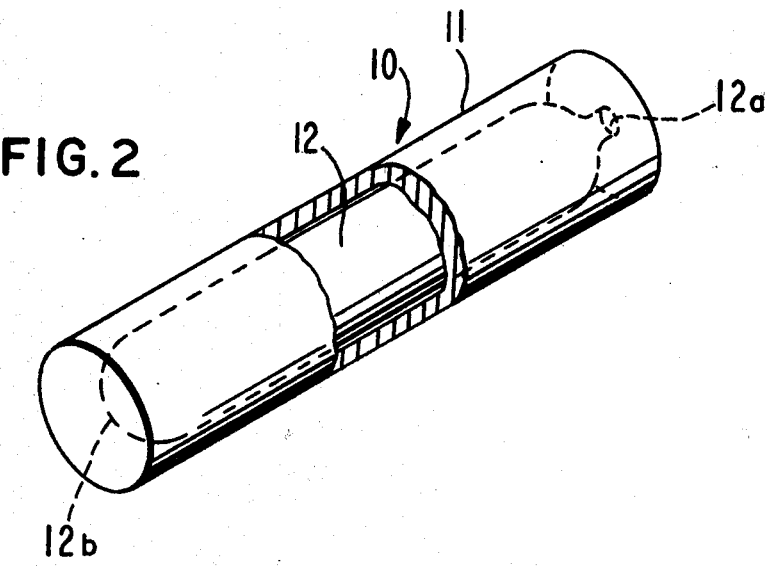
FIG. 2 illustrates the dispenser in opened-section with a portion of its wall removed for depicting the structure of the dispenser.

FIG. 2 is a view of dispenser 10 with a section of wall 11 removed for depicting wall 11 and container 12 forming the dispenser. Wall 11 is made from a material that imparts physical integrity and support to dispenser 10 throughout the dispensing period, and possesses the ability when activated by an exterior fluid to provide the driving force needed for operating dispenser 10. Wall 11 is structurally a hydrogel laminate comprising (1) a layer of a cross-linked hydrophilic polymer grafted to (2) a layer of a noncross-linked hydrophilic polymer. The laminate is made by (a) polymerizing a monoethylenically unsaturated monomer to form a layer of a homogenous hydrophilic polymer, and then (b) polymerizing onto the layer a mixture of a monoethylenically unsaturated monomer and a cross-linking monomer containing at least two ethylenic double bonds to form a layer of a porous, cross-linked hydrophilic polymer. The hydrophilic polymer (a) is grafted to the cross-linked hydrophilic polymer (b) by the mixture of monomers (b) penetrating into polymer (a) during the polymerization of polymer (b). A further benefit is polymer (a) becomes insoluble in fluids.

The monomer mixture for forming the cross-linked hydrophilic polymer can consist of a hydrophilic monomer such as glycol monomethacrylate containing 0.01% to 5% by weight of a cross-linking agent, and an initiator for the polymerization reaction. Other hydrophilic monomers such as acrylate, acrylamide and methacrylamide, and acrylonitrile with sodium methacrylate or acrylate, and the like can be used in the polymerization synthesis. The cross-linking monomers useful for the present purpose include glycol bis-methacrylates and acrylates, N, $N^1$-methylene-bis-methacrylamide, triacrylol perhydrotriazine, and the like. Initiators include soluble persulfates such as ammonium persulfate, azo initiators such as azo-bis-isobutyronitrile, and the like. For synthesizing the homogenous, hydrophilic polymer, noncross-linked methacrylates, noncross-linked acrylates and the like can be used for forming the layer. Procedures for polymerization of the polymers are disclosed in Great Britain Pat. No. 1,246,179. In a presently preferred embodiment, the hydrogel wall-laminate surrounding container 12 has the hydrophilic polymer layer (a) facing the container, and cross-linked hydrophilic polymer layer (b) positioned distant from container 12 and facing the environment of use. The layers can have the same or different thickness, generally from 0.01 mm to 7 mm per layer, or more.

Figure 3:
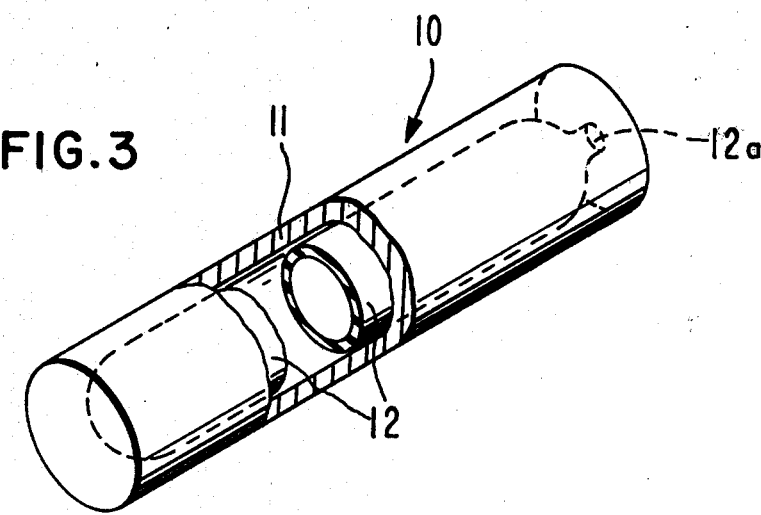
FIG. 3 is a view similar to FIG. 2 for further illustrating structural embodiments of the dispenser.

FIG. 3 is a view of dispenser 10 with a section of wall 11 removed for illustrating container 12. Container 12 is also seen in opened-section and it has a passageway 12a for releasing fluids and agents from container 12. Container 12 is made from a material that can house a fluid, an agent, or a mixture thereof substantially free from any adverse effects on the contents of container 12. The container can also house its contents over a prolonged period of time sheltered from any possible adverse actions present in the environment of use. Passageway 12a is preferrably formed during manufacture of container 12, and it has internal dimensions that assist in governing the rate of release of its contents from container 12.

Container 12 is made from an elastomeric, or other low-modulus material, that can decrease its dimensions over time, and more particularly, collapse in response to pressure applied against its exterior surface as wall-laminate 11 absorbs fluid and expands. Typical elastomeric polymers include natural rubber, often identified by the synonyms poly(2-methyl-1,3-butadiene) and cis-1,4-polyisoprene, gutta percha or trans-polyisoprene, cyclized rubber, silicone rubber, synthetic isoprene rubber, butadiene rubber, copolymeric styrene-butadiene rubbers, nitrile rubber, chloroprene rubber, ethylene-propylene rubbers, butyl rubbers, and the like. These elastomeric materials are disclosed in *Handbook of Common Polymers*, by Scott and Roff, Sections 29 through 40, 1971, published by the Chemical Rubber Co., Cleveland, Ohio. Container 12, formed from the above representative materials, can have a wall of varying thickness, usually about 0.001 mm to 7 mm, or more depending on the container, and the use of dispenser 10.

Figure 4:
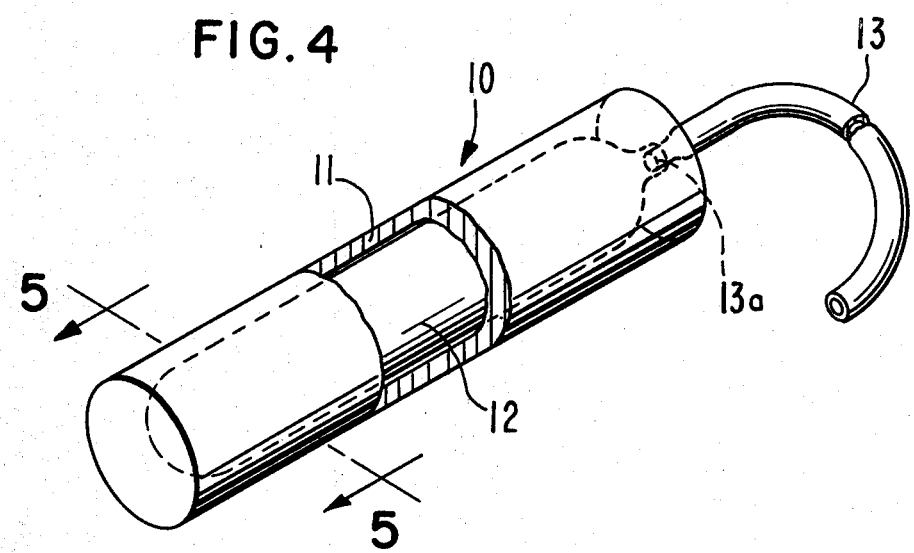
FIG. 4 is a view of the dispenser made with a releasable attachment for delivering fluid or agent to environments of use distant from the dispenser; and, FIG. 5 illustrates the wall-laminate defining a structural member of the dispenser, taken through 4—4 of FIG. 4.

FIG. 4 is a side view similar to FIGS. 1 through 3 with dispenser 10 in FIG. 4 fabricated for receiving a tube 13 that conveys the contents ejected from dispenser 10 to a point of use.

The contents that can be housed and delivered by dispenser 10 include fluids such as water, saline, plasma and the like. Typical agents that can be administered include algicides, anti-oxidants, air-purifiers, biocides, bactericides, catalysts, chemical reactants, cosmetics, disinfectants, drugs, fungicides, flavoring agents, foods, food supplements, fertility inhibitors, fermentation agents, fertility promoters, germicides, insecticides, microorganism alternators, nutrients, pesticides, plant growth promoters, plant growth inhibitors, preservating agents, slimicides, surfactants, sterilization agents, sex sterilants, vitamins, and other like useful and beneficial agents that benefit animals including man.

Exemplary drugs that can be administered according to the spirit of the invention include locally and systemically acting drugs. These drugs include a member selected from the group consisting of physiologically and pharmacologically acting drugs such as gastrointestinal administrable drugs, central nervous system acting drugs, hypnotic, sedative, psychic energizer, tranquilizer, anticonvulsant, anti-parkinson, muscle relaxant, analgesic, antipyretic, anti-inflammatory, anesthetic, antispasmodic, antimicrobial, antiviral, antiulcer, hormonal, sympathomimetic, diuretic, hypoglycemic, vitamins, contraceptive and ophthalmic drugs. These beneficial drugs and their dose amounts for humans are known to the art in *Drills' Pharmacology in Medicine*, edited by DiPalma, 1965, published by Mc-Graw-Hill Book Company, New York, in *Pharmacological Basis of Therapeutics*, by Goodman and Gilman, 4th Ed., 1970, published by MacMillan Co., London, and in U.S. Pat. No. 3,977,404. The drug in the container can be mixed with a pharmaceutically acceptable liquid such as water, saline, cottonseed oil, sesame oil, ethylene oleate, isopropyl myristate, propylene glycol, and the like. The drug can be present in solution, in semi-solid or paste formulation, in a thixotropic state, and the like. Pharmaceutically acceptable carriers and the like are known to the dispensing art in *Remington's Pharmaceutical Science*, 14th Ed., pages 1461 59 1762, 1970, published by the Mack Publishing Co., Easton, PA.

Figure 5:
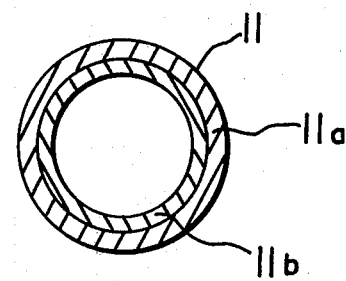

FIG. 5 illustrates a view taken through 4—4 of FIG. 4. FIG. 5 shows wall 11 comprising a layer of a cross-linked hydrophilic polymer 11a and a layer of a homogenous hydrophilic polymer 11b, grafted to polymer 11a. In operation, fluid is absorbed by both polymer 11a and polymer 11b, with polymer 11b expanding mainly inwardly against container 12, thereby squeezing container 12 causing is to eject its contents through passageway 12a to the environment of use.

An improved dispenser is manufactured by following the specification as follows: first, a cylindrical shaped container 4.0 cm long, 3.8 mm inside diameter and 4.8 mm outside diameter, is injection molded at 180° C., at 77–84 Kg/cm$^2$, from an elastomeric copolymer styrenebutadiene. Next, a mandrel is inserted into the container, and this assembly placed in a two-piece cavity mold. Then, the mold is charged with a 10% solution of noncross-linked ethylene glycol monomethacrylate polymer in a mixture of 80% ethanol and 20% water, and the solvents evaporated to form a 0.4 mm polymer layer. Then the mold is removed and replaced with larger mold, and the assembly heated to 60° C. and the mold charged with a monomer mixture of 30% ethylene glycol monomethacrylate, 1% bis-methacrylate and 69% of a 10% solution of ammonium persulfate in distilled water. The mold is covered, and placed in a carbon dioxide environment, with polymerization completed in about 15 minutes. The mold is then cooled and the mold removed at room temperature. The outer cross-linked polymer layer is firmly bonded to the inner layer that faces the container, and the outer layer is about 5 times thicker than the inner layer.

In another embodiment the wall can be formed as a pair of molds having when joined dimensions corresponding to the total exterior dimensions of the container. In this embodiment, the molds are first charged with a layer of polymeric ethylene glycol monomethacrylate and a layer of copolymeric ethylene glycol monomethacrylate and ethylene glycol bis-methacrylate. The laminates are removed from the molds, placed around a container, and their surfaces joined by adhesive bonding to yield a strong wall. The adhesives that can be used include glues, starches, oxidized starches, chlorinated starches, natural rubber-based adhesives, styrene-butadiene rubber adhesive, nitrile rubber adhesive, phenolic adhesive, amino resin adhesives, silicone rubber adhesives, epoxy resin adhesives, acrylic ester adhesives, and the like. Suitable adhesives and procedures for using adhesives are disclosed in *Adhesion And Bonding* by Norbet M. Bikales, 1971, published by Wiley-Interscience, New York.

The containers in the above embodiments can be charged with saline, tetracycline hydrochloride in polyethylene glycol 200, ephinephrine hydrochloride in buffer, for delivery to a receptor site. And, while the above presentation is illustrative of various dispensers that can be provided by the invention, it is to be understood these dispensers are not to be construed as limiting, as they can take a wide variety of shapes, sizes and forms adapted for delivering a fluid, an agent, or a mixture thereof. For example, the dispenser can be manufactured for dispensing drug to animals, which term includes warm-blooded mammals, humans, household, sport, farm and zoo animals. The dispenser can be used for dispensing drugs to avians, pisces and reptiles. The dispenser can be sized, shaped, and adapted for dispensing drugs to body cavities, body openings, for oral administration, for use as intramuscular implants, intrauterine, vaginal, cervical, rectal, nasal, ear, ocular, and dermal applications. The dispenser can also be used as an artificial gland, and arterial and venous administration of drugs. The dispenser can be used in commerce broadly including in homes, hospitals, nursing homes, ships, laboratories, factories, and the like.

Although the foregoing has been described in details by way of illustration of presently preferred embodiments for the purpose of clarity of understanding, it will be understood that certain changes and modifications may be practiced without departing from the scope and spirit of the invention.

I claim:

1. A dispenser comprising: a housing formed of a laminate comprising a layer of a cross-linked hydrophilic polymer grafted to a layer of a noncross-linked hydrophilic polymer; a container within the housing, said container made of a material changeable from a storing capacity to a substantially emptied capacity over time; an outlet mean in the container that communicates with the container and the exterior of the dispenser, and wherein, when the dispenser is in operation in the environment of use, the dispenser releases its contents in response to the laminate absorbing fluid from the environment and expanding, thereby exerting pressure on the container which changes from a storing capacity to a substantially emptied capacity and dispenses its contents through the outlet means from the dispenser.

2. The dispenser of claim 1 wherein the container is charged with a fluid.

3. The dispenser of claim 1 wherein the container is charged with a beneficial agent.

4. The dispenser of claim 1 wherein the cross-linked hydrophilic polymer is formed from a mixture of a monoethylenically unsaturated monomer and a crosslinking monomer containing at least two ethylenic double bonds.

5. The dispenser of claim 1 wherein the hydrophilic polymer is homogenous and a noncross-linked polymer, and is formed from a monoethylenically unsaturated monomer.

6. The dispenser of claim 1 wherein the container contains a drug, which drug is present in solution, in semi-solid, or in a thixotropic formulation.

7. The dispenser of claim 1 wherein the dispenser is sized, shaped and adapted for oral use.

8. The dispenser of claim 1 wherein the dispenser is sized, shaped and adapted for vaginal use.

9. The dispenser of claim 1 wherein the dispenser is sized, shaped and adapted for ano-rectal use.

10. The dispenser of claim 1 wherein the dispenser is sized, shaped and adapted for use as an implant.

11. The dispenser of claim 1 wherein the container is made of a member selected from the group consisting of natural rubber, gutta percha, cyclized rubber, silicone rubber, isoprene rubber, butadiene rubber, styrenebutadiene rubber, nitrile rubber, chloroprene rubber, ethylene-butylene rubber, and butyl rubber.

12. The dispenser of claim 1 wherein the container is connected to a conduit leading to a distant site.

* * * * *